United States Patent
Bhirud et al.

(10) Patent No.: US 9,695,159 B2
(45) Date of Patent: Jul. 4, 2017

(54) PROCESS FOR PREPARATION OF CANAGLIFLOZIN

(71) Applicant: Glenmark Pharmaceuticals Limited, Mumbai (IN)

(72) Inventors: Shekhar Bhaskar Bhirud, Mumbai (IN); Samir Naik, Thane (IN); Sachin Srivastava, N. Mumbai (IN); Dinesh Deore, Thane (IN); Sukumar Sinha, N. Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/313,243

(22) PCT Filed: May 22, 2015

(86) PCT No.: PCT/IB2015/053780
§ 371 (c)(1),
(2) Date: Nov. 22, 2016

(87) PCT Pub. No.: WO2015/181692
PCT Pub. Date: Dec. 3, 2015

(65) Prior Publication Data
US 2017/0114051 A1    Apr. 27, 2017

(30) Foreign Application Priority Data

May 27, 2014  (IN) .......................... 1766/MUM/2014

(51) Int. Cl.
C07D 409/10    (2006.01)
C07D 333/16    (2006.01)

(52) U.S. Cl.
CPC ......... *C07D 409/10* (2013.01); *C07D 333/16* (2013.01)

(58) Field of Classification Search
CPC ............................ C07D 409/10; C07D 333/16
See application file for complete search history.

(56) References Cited

U.S. PATENT DOCUMENTS

| 2010/0099883 A1 | 4/2010 | Fillers et al. |
| 2014/0105839 A1* | 4/2014 | Deliencourt-Godefroy ............ C07C 43/225 424/62 |

FOREIGN PATENT DOCUMENTS

| CN | 102115468 A | 7/2011 | |
| CN | 103694230 A | 4/2014 | |
| CN | WO 2015139386 A1 * | 9/2015 | ........... C07D 409/10 |
| WO | 2005012321 A1 | 2/2005 | |
| WO | 2013064909 A2 | 5/2013 | |

OTHER PUBLICATIONS

WO 2015139386 A1 English Machine Translation, ProQuest Dialog Mar. 10, 2017 p. 1-49.*

* cited by examiner

*Primary Examiner* — Samantha Shterengarts
*Assistant Examiner* — Matt Mauro
(74) *Attorney, Agent, or Firm* — Ryan, Mason & Lewis, LLP

(57) ABSTRACT

The present invention relates to a process for the preparation of canagliflozin and intermediates thereof.

9 Claims, 3 Drawing Sheets

PROCESS FOR PREPARATION OF CANAGLIFLOZIN

PRIORITY

This application claims priority under 35 U.S.C. §371 to International Application No. PCT/IB2015/053780, filed May 22, 2015 which claims the benefit of Indian Provisional Application No. 1766/MUM/2014, filed May 27, 2014, and entitled "PROCESS FOR PREPARATION OF CANAGLIFLOZIN" the contents of which are incorporated by reference herein.

FIELD OF INVENTION

The present invention relates to process of preparation of canagliflozin.

BACKGROUND OF THE INVENTION

Canagliflozin which is chemically known as 1(S)-1,5-anhydro-1-[3[[5-(4-fluorophenyl)-2-thienyl]methyl]-4-methylphenyl]-D-glucitol, is represented by a compound of formula I,

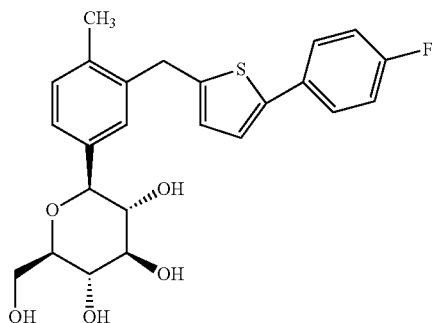

I

Canagliflozin, is a sodium-glucose co-transporter 2 (SGLT2) inhibitor indicated as an adjunct to diet and exercise to improve glycemic control in adults with type 2 diabetes mellitus.

BRIEF DESCRIPTION OF THE ACCOMPANYING FIGURES

Figure 1:
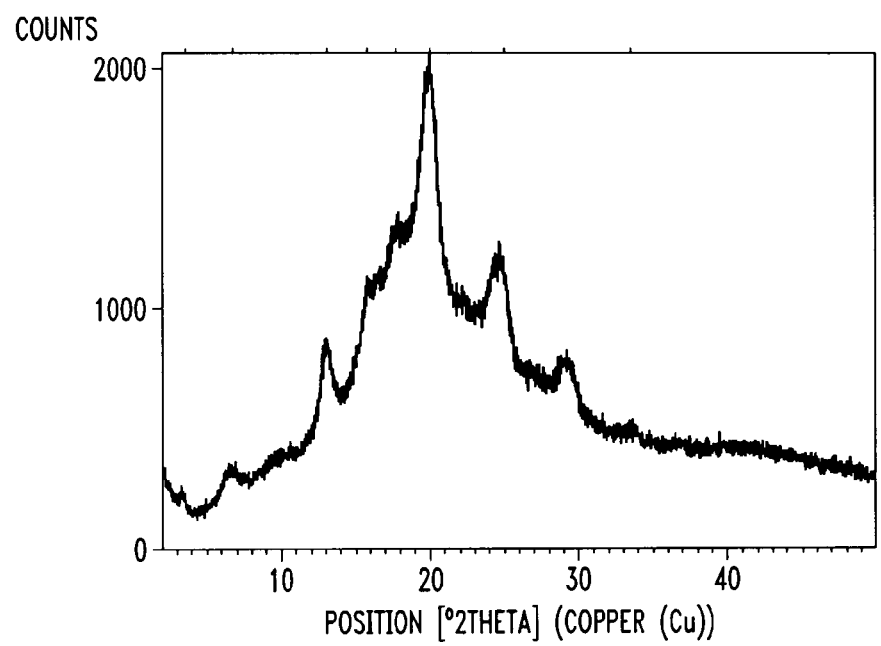
Figure 2:
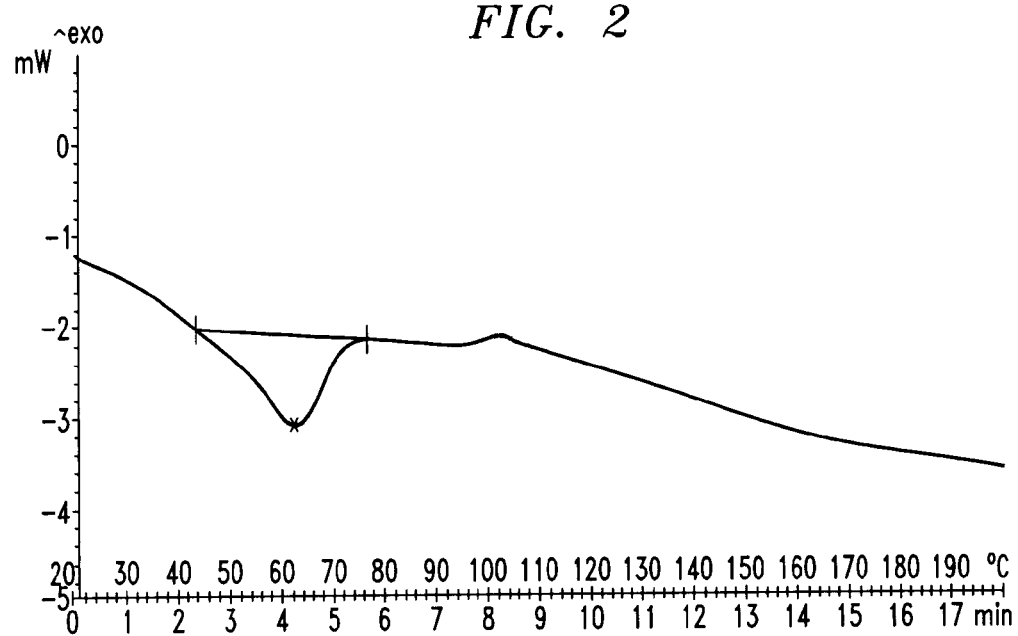
Figure 3:
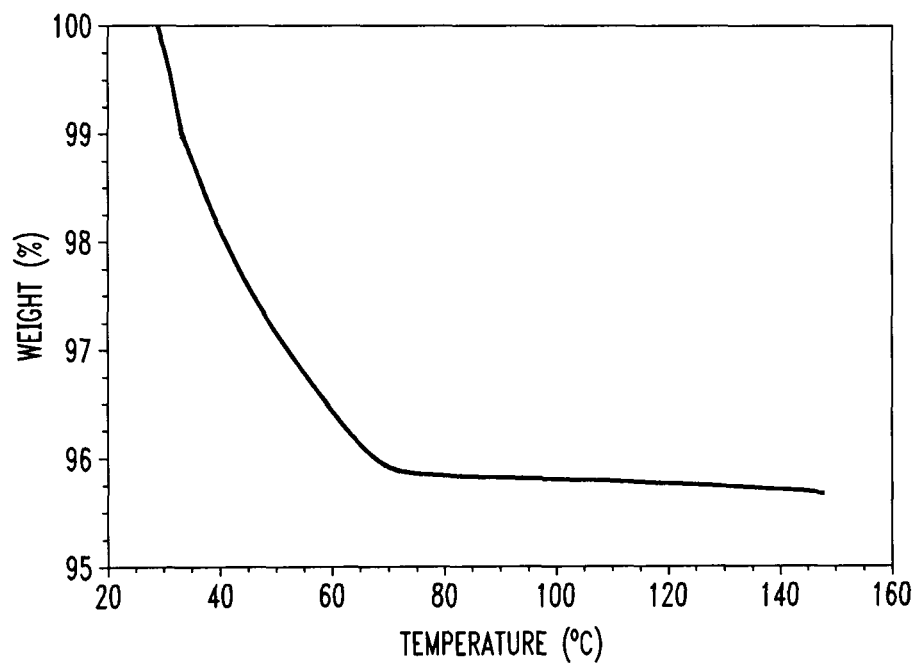
Figure 4:
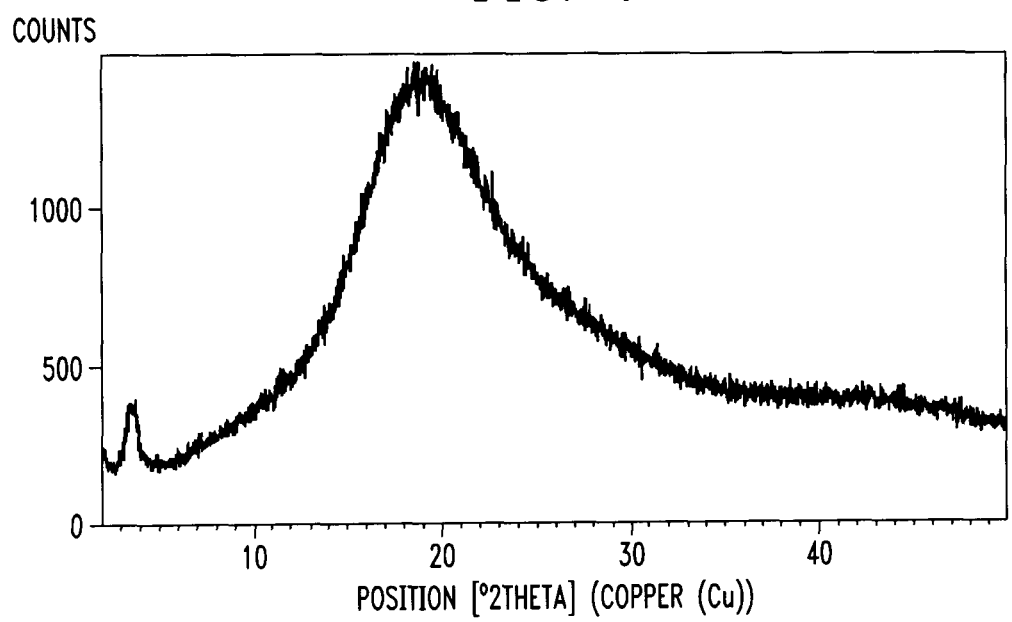
Figure 5:
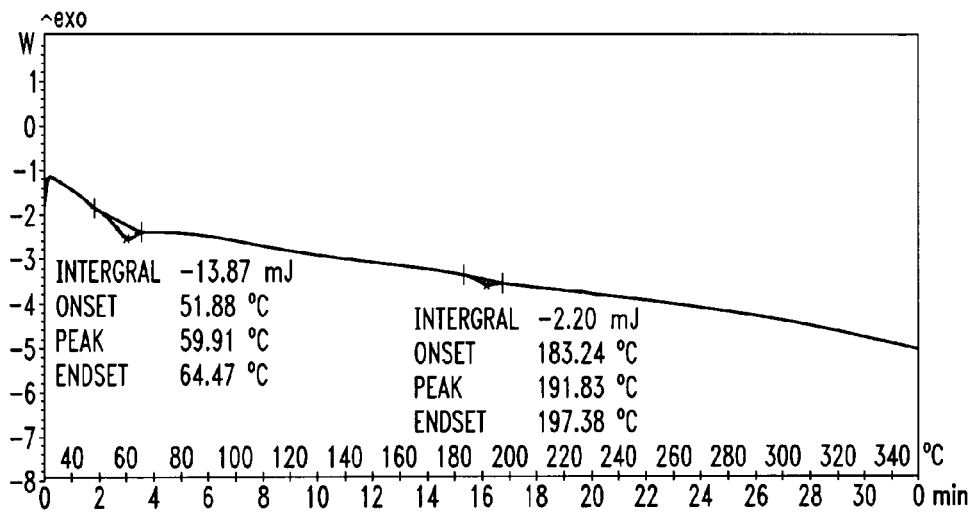
Figure 6:
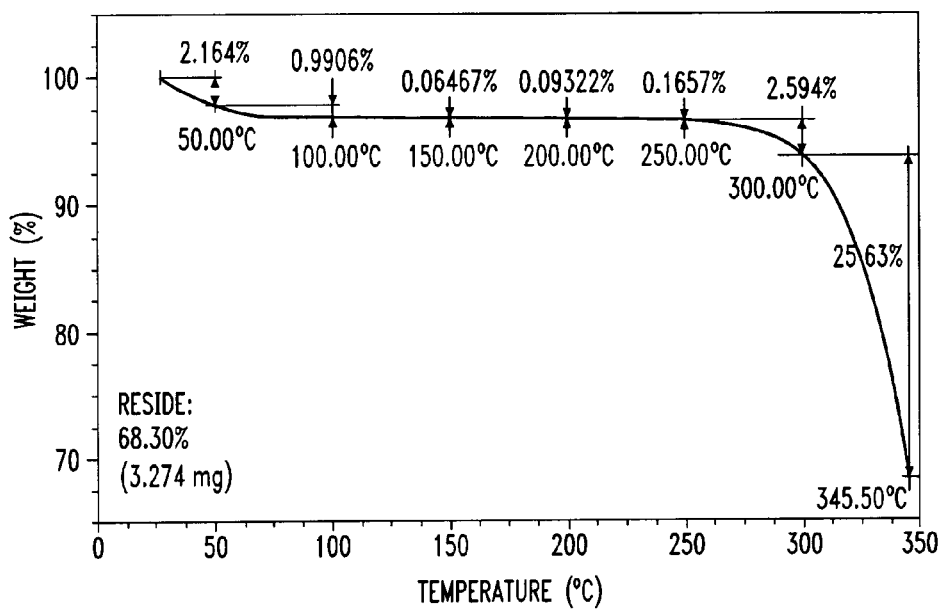

FIG. 1: PXRD pattern of crystalline canagliflozin monohydrate, as obtained in example 8.
FIG. 2: DSC of crystalline canagliflozin monohydrate, as obtained in example 8.
FIG. 3: TGA of crystalline canagliflozin monohydrate, as obtained in example 8.
FIG. 4: PXRD of amorphous canagliflozin, as obtained in example 15.
FIG. 5: DSC of amorphous canagliflozin, as obtained in example 15.
FIG. 6: TGA of amorphous canagliflozin, as obtained in example 15.

SUMMARY OF THE INVENTION

In one embodiment, the present invention provides a process for the preparation of canagliflozin, a compound of formula I comprising:

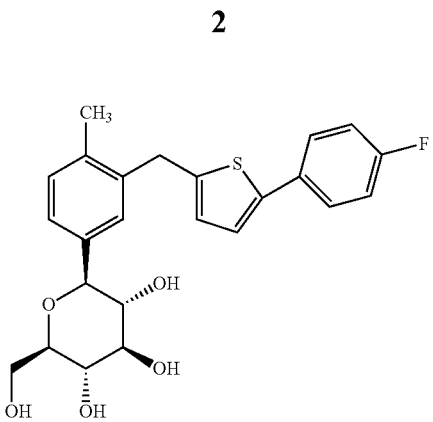

I a) reacting a compound of formula II with a reducing agent;

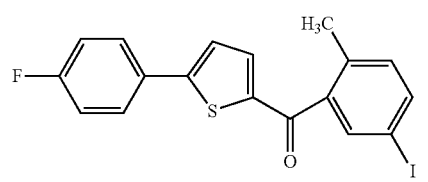

II

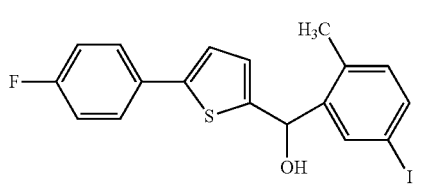

III to obtain a compound of formula III;

b) coupling the compound of formula III with a compound of formula IV

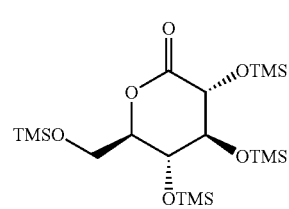

IV

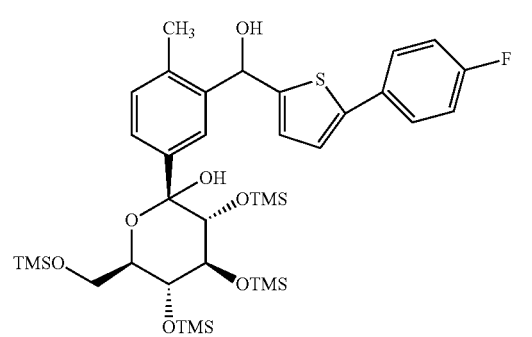

V to obtain a compound of formula V;

c) converting the compound of formula V to a compound of formula VI; and

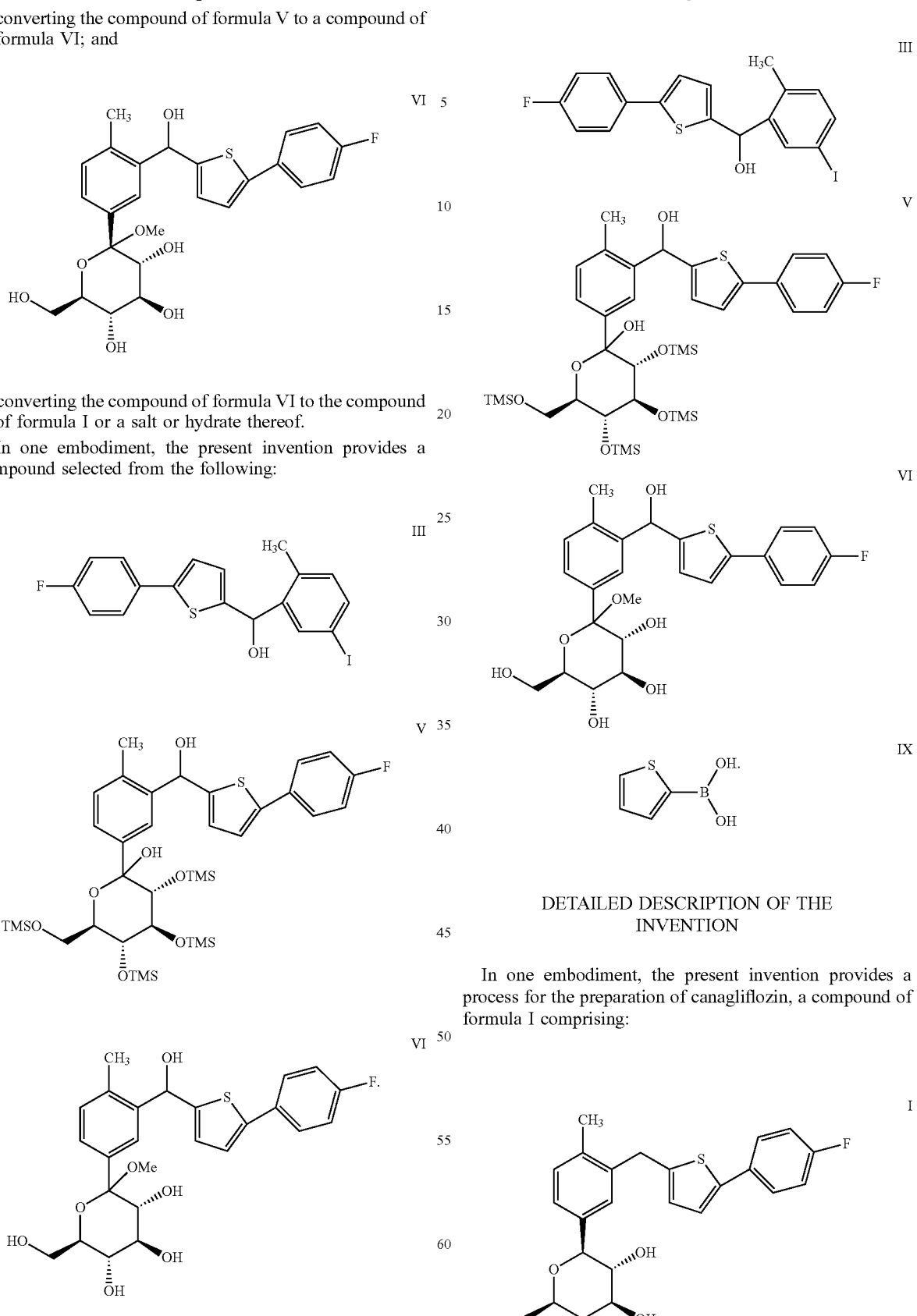

d) converting the compound of formula VI to the compound of formula I or a salt or hydrate thereof.

In one embodiment, the present invention provides a compound selected from the following:

In one embodiment, the present invention provides a process for the preparation of canagliflozin by using a compound selected from the group consisting of

DETAILED DESCRIPTION OF THE INVENTION

In one embodiment, the present invention provides a process for the preparation of canagliflozin, a compound of formula I comprising:

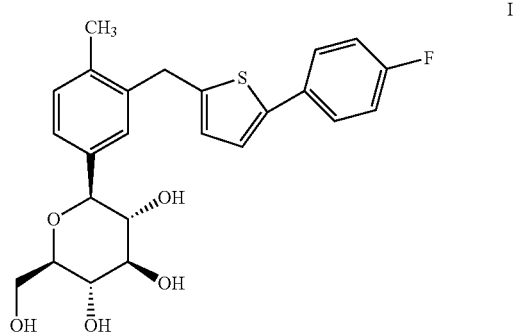 [SMILES: Cc1ccc([C@@H]2O[C@H](CO)[C@@H](O)[C@H](O)[C@H]2O)cc1Cc1ccc(-c2ccc(F)cc2)s1]

a) reacting a compound of formula II with a reducing agent

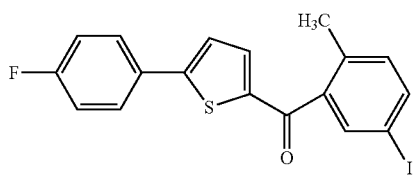

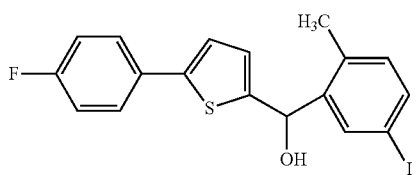

to obtain a compound of formula III;
b) coupling the compound of formula III with a compound of formula IV

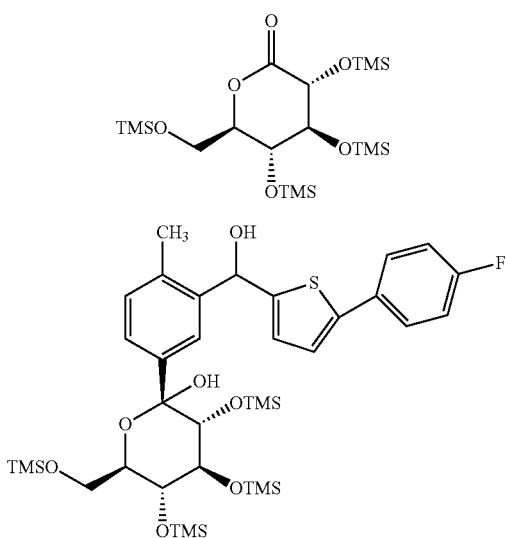

to obtain a compound of formula V;
c) converting the compound of formula V to a compound of formula VI; and

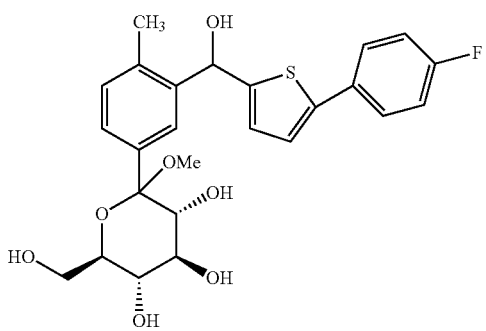

d) converting the compound of formula VI to the compound of formula I.

In one embodiment, in step a) of the above process, compound of formula II is reduced to a compound of formula III in the presence of a reducing agent.

In one embodiment, reducing agent may be selected from the group consisting of diborane, diazene, metal hydrides such as sodium borohydride, potassium borohydride, lithium aluminium hydride, diisobutyl aluminium hydride, aluminum hydride and the like. Preferably the reducing agent is sodium borohydride.

In one embodiment, the reduction of the compound of formula II may be carried out in presence or absence of a solvent.

In one embodiment, solvent may be selected from the group consisting of alcohols such as methanol, ethanol, n-propanol, isopropanol, n-butanol, isobutanol and the like; chlorinated solvents such as methylene dichloride, ethylene dichloride, chloroform, carbon tetrachloride and the like; amides such as dimethyl formamide, dimethyl acetamide and the like; sulfoxides such as dimethyl sulfoxides and the like; hydrocarbons such as hexane, toluene, xylene, cyclohexane, n-heptane and the like; ethers such as diethyl ether, methyl-tertiary butyl ether, diisopropyl ether, tetrahydrofuran and the like or mixtures thereof. Preferably, the solvent is a mixture of methylene dichloride and methanol.

In one embodiment, the compound of formula II is reduced to the compound of formula III in the absence of a lewis acid.

In one embodiment, the compound of formula II is reacted with sodium borohydride in the presence of methylene dichloride and methanol.

In one embodiment, the compound of formula II is reacted with sodium borohydride in the presence of methanol.

In one embodiment, the reduction of compound of formula II is carried out at a temperature of about 25-30° C.

In one embodiment, the compound of formula II is reacted with sodium borohydride in the presence of methylene dichloride and methanol in the absence of a lewis acid.

In one embodiment, the compound of formula II is reacted with sodium borohydride in the presence of methanol in the absence of a lewis acid.

In one embodiment, the compound of formula III is isolated from the reaction mixture by methods such as filtration, distillation and the like. Preferably, the compound of formula III is isolated by distillation.

In one embodiment, optionally, the compound of formula III is purified by treating the compound of formula III with a solvent.

The term "treating" refers to contacting, slurrying, dissolving or suspending.

In one embodiment, the solvent for purification may be selected from the group consisting of hydrocarbons such as cyclohexane, hexane, toluene, xylene, n-heptane and the like; alcohols such as methanol, ethanol, isopropanol, propanol, butanol, and the like. Preferably the solvent is n-heptane.

In one embodiment, the compound of formula III is slurried in n-heptane and isolated by filtration or centrifugation. Preferably, the compound of formula III is isolated by filtration.

In one embodiment, the present invention provides compound of formula III characterized by 1HNMR having peaks at 2.18, 5.97, 6.29, 6.79, 6.94, 7.16-7.26, 7.52, 7.58-7.62, 7.85.

In one embodiment, in step b) of the above process, the compound of formula III is coupled with a compound of formula IV to obtain a compound of formula V.

In one embodiment, the coupling reaction may be carried out by reacting the compound of formula III with a proton abstracting agent followed by reaction with the compound of formula IV. Proton abstracting agents are generally strong bases such as n-butyl lithium, sec-butyl lithium, sodium hydride, potassium hydride, isopropylmagnesium chloride-lithium chloride complex in tetrahydrofuran. Preferably, the base used is n-butyl lithium.

In one embodiment, the coupling reaction may be carried out by reacting the compound of formula III with a Grignard reagent followed by reaction with the compound of formula IV.

In one embodiment, the compound of formula III is reacted with a base followed by adding the compound of formula IV.

In one embodiment, the mixture of the compound of formula III with a base is added to the compound of formula IV.

In one embodiment, base is added to a mixture of the compound of formula III and the compound of formula IV.

In one embodiment, the present invention provides process for the preparation of compound of formula V comprising reacting the compound of formula III with the compound of formula IV in the presence of a base characterized in that the base is added in one lot to a mixture of compound of formula III and IV.

Surprisingly, it is noted that the addition of base to the mixture of the compound of formula III and the compound of formula IV results in better yield.

In one embodiment, in step b) of the above process the coupling reaction is carried out by the addition of a strong base to a mixture of the compound of formula III and the compound of formula IV in a solvent.

In one embodiment, in step b) of the above process the coupling reaction is carried out by adding n-butyl lithium to a mixture of compound of formula III and IV in a solvent.

The solvent may be selected from the group consisting of water, alcohols such as methanol, ethanol, propanol, isopropanol, n-butanol and the like; amides such as dimethyl acetatmide, N, N-dimethyl formamide and the like; hydrocarbons such as cyclohexane, hexane, toluene, xylene, n-heptane and the like; chlorinated solvents such as methylene dichloride, ethylene dichloride, chloroform, carbon tetrachloride and the like; ethers such as diethyl ether, diisopropyl ether, methyl-tertiary butyl ether, tetrahydrofuran and the like; esters such as ethyl acetate, isopropyl acetate and the like or mixtures thereof. Preferably, the solvent is a mixture of toluene and tetrahydrofuran.

In one embodiment, the coupling of the compound of formula III and the compound of formula IV is carried out by adding n-butyl lithium in hexane to a mixture of compound of formula III and compound of formula IV present in a mixture of tetrahydrofuran and toluene.

In one embodiment, the coupling of the compound of formula III and the compound of formula IV may be carried out at a temperature of about −100 to 5° C. Preferably, the reaction is carried out at a temperature of about −60 to about −80° C.

In one embodiment, the reaction transpires over a period of about 30 minutes to about 3 hrs. Preferably, the reaction transpires over a period of about 1.5 to 2.5 hrs.

In one embodiment, the compound of formula V may be isolated by methods such as filtration, distillation and the like.

In one embodiment, in step c) of the above process, the compound of formula V is converted to the compound of formula VI.

In one embodiment, the compound of formula V is converted to the compound of formula VI in presence of an acid.

In one embodiment, the compound of formula V may not be isolated in step b) and in-situ converted to the compound of formula VI.

In one embodiment, the compound of formula III is coupled with the compound of formula IV to obtain the compound of formula VI without isolating the compound of formula V.

In one embodiment, in step c) of the above process the conversion of compound of formula V to compound of formula VI may be carried out by treating the compound of formula V with a suitable acid in methanol.

In one embodiment, the suitable acids for conversion of the compound of formula V to the compound of formula VI may be selected from the group consisting of acids such as hydrochloric acid, sulfuric acid, methane sulphonic acid, camphor sulfonic acid, p-toluene sulfonic acid and the like. Preferably the acid used is methane sulphonic acid.

In one embodiment, the conversion of the compound of formula V to the compound of formula VI is carried out using methane sulphonic acid in methanol.

In one embodiment, the addition of methane sulphonic acid in methanol to a reaction mixture containing the compound of formula V is carried out at a temperature of about −60 to −70° C.

In one embodiment, the reaction transpires at a temperature of about 20 to about 35° C. over a period of about 10 to about 30 hrs. Preferably, the reaction transpires at a temperature of about 25 to 30° C. over a period of about 15 to 20 hrs.

In one embodiment, the compound of formula VI may be isolated by methods such as distillation, concentration and the like. Preferably the compound of formula VI is isolated by distillation.

In one embodiment, the compound of formula VI obtained after distillation is purified in a solvent.

In one embodiment, the compound of formula VI is purified by a process comprising:
i) treating the compound of formula VI with a solvent;
ii) optionally, mixing with an anti-solvent; and
iii) isolating the compound of formula VI.

In one embodiment, in step i) of the above process the compound of formula VI is treated with a solvent.

In one embodiment, in step i) of the above process the compound of formula VI is treated with a solvent to obtain a solution.

The solvent may be selected from the group consisting of alcohols such as methanol, ethanol, propanol, isopropanol, n-butanol and the like; halogenated solvents such as methylene dichloride, ethylene dichloride, chloroform, carbon tetrachloride and the like; amides such as dimethyl formamide, dimethyl acetamides and the like; ketones such as acetone, methyl ethyl ketone, methyl isobutyl ketone and the like; esters such as ethyl acetate, butyl acetate, isopropyl acetate and the like; nitriles such as acetonitrile, propionitrile and the like; ethers such as diethyl ether, diisopropyl ether, tetrahydrofuran and the like; hydrocarbons such as hexane, toluene, xylene, cyclohexane, heptane and the like or mixtures thereof. Preferably, the solvent is methylene dichloride or toluene.

In one embodiment, in step ii) of the above process the anti-solvent may be selected from the group consisting of water, hexane, ethyl acetate and the like; Preferably, the anti-solvent is hexane.

In one embodiment, in step ii) of the above process, the compound of formula VI in methylene dichloride is mixed with hexane.

In one embodiment, the reaction mixture containing the compound of formula VI in methylene dichloride and hexane is stirred for a period of about 30 min to about 3 hrs. Preferably, the reaction mixture is stirred for a period of about 1 to 2 hrs.

In one embodiment, in step iii) of the above process the purified compound of formula VI is isolated by filtration, centrifugation and the like.

In one embodiment, the present invention provides compound of formula VI characterized by 1HNMR having peaks at 2.24, 2.9, 3.55, 3.75, 4.53, 4.66-4.70, 4.96, 5.68, 6.82, 6.91, 7.14-7.24, 7.35, 7.60-7.65.

In one embodiment, in step d) of the above process, the compound of formula VI is converted to the compound of formula I by treating with a reducing agent.

In one embodiment, in step d) of the above process, the compound of formula VI is not isolated in step 'c' and converted in-situ to the compound of formula I.

In one embodiment, the reducing agent is a silane reagent such as triethyl silane.

In one embodiment, reduction is carried out in the presence of a lewis acid such as boron trifluoride.diethyl ether complex, boron trifluoride, tetrahydrofuran complex, aluminium chloride, zinc chloride and the like.

In one embodiment, in step d) of the above process, the compound of formula VI is converted to the compound of formula I by treating with triethyl silane in the presence of boron trifluoride.diethyl ether complex.

In one embodiment, the conversion of the compound of formula VI to the compound of formula I may be carried out in a solvent.

In one embodiment, solvent may be selected from the group consisting of nitriles such as acetonitrile, propionitrile and the like; chlorinated solvents such as methylene dichloride, ethylene dichloride, chloroform and the like; hydrocarbons such as heptane, hexane, toluene, xylene and the like; ethers such as diethyl ether, diisopropyl ether and the like; alcohols such as methanol, ethanol, propanol, isopropanol, n-butanol and the like; esters such as ethyl acetate, isopropyl actetate, butyl acetate and the like. Preferably, the solvent is methylene dichloride.

In one embodiment, in step d) of the above process triethyl silane is added to the compound of formula VI in methylene dichloride.

In one embodiment, the addition is carried out at a temperature of about −100 to 50° C. Preferably, the addition is carried out at a temperature of about −60 to −70° C.

In one embodiment, the addition is carried out at a temperature of about 25-35° C.

In one embodiment, the addition of boron trifluoride.diethyl ether complex is carried out at a temperature of about −100 to 5° C. Preferably, the addition is carried out at a temperature of about −70 to −80° C.

In one embodiment, the reaction transpires at a temperature of about −5 to 25° C. over a period of about 1 to 5 hrs. Preferably, the reaction transpires at a temperature of about 0-5° C. over a period of 2 to 3 hours.

In one embodiment, on completion of conversion of the compound of formula VI to the compound of formula I, the reaction mixture is basified using a base.

In one embodiment, base may be selected from organic or an inorganic base. The inorganic base may be selected from but is not limited to hydroxides such as sodium hydroxide, potassium hydroxide; carbonates such as sodium carbonate, potassium carbonate; bicarbonates such as sodium bicarbonate, potassium bicarbonate, alkoxides such as sodium methoxide, potassium tertiary butoxide, hydrides such as sodium hydride; organic base such as triethyl amine, trimethyl amine, pyridine, dimethyl amino pyridine. Preferably, the base is sodium bicarbonate.

In one embodiment, the compound of formula I may be optionally treated with charcoal, filtered and then isolated from the reaction mixture by concentrating or distilling the organic layer.

In one embodiment, the compound of formula I is treated with a solvent selected from the group consisting of esters such as ethyl acetate, isopropyl acetate and the like; amides such as dimethyl acetamide, dimethyl formamide and the like; ketones such as acetone, methyl ethyl ketone, methyl isobutyl ketone and the like; nitriles such as acetonitrile, propionitrile and the like; chlorinated solvents such as methylene dichloride, ethylene dichloride, chloroform and the like; ethers such as diethyl ether, diisopropyl ether, tetrahydrofuran, methyl tertiary butyl ether and the like, water or mixtures thereof. Preferably, the compound of formula I is treated with ethyl acetate.

In one embodiment, the compound of formula I in ethyl acetate is subjected to charcoal treatment, filtered and then isolated by distillation, centrifugation or filtration.

In one embodiment, the present invention provides a process for the preparation of crystalline canagliflozin (1-S) comprising:
a) treating canagliflozin with an organic solvent to obtain a mixture;
b) optionally, heating the mixture of step 'a';
c) adding water to the mixture of step 'b' wherein the amount of water is more than 2 molar equivalent with respect to canagliflozin,
d) adding an anti-solvent; and
e) cooling and isolating crystalline canagliflozin (1-S).

In one embodiment, in step 'a' of the above process the solvent may be selected from the group consisting of halogenated solvents such as dichloromethane, dichloroethane, chloroform, carbon tetrachloride and the like, hydrocarbons such as n-hexane, n-heptane, cyclohexane, benzene, toluene, xylene and the like; esters such as methyl acetate, ethyl acetate, isopropyl acetate, tertiary butyl acetate and the like; ethers such as diethyl ether, diisopropyl ether, methyl tertiary butyl ether and the like; and mixtures thereof. Preferably, the solvent is ethyl acetate.

In one embodiment, in step 'b' of the above process the mixture of canagliflozin in a solvent is heated to 0° C. to reflux temperature of the solvent. The mixture may be heated to a temperature of about 35-50° C. to obtain a solution.

In one embodiment, in step 'c' of the above process more than two equivalents of water is added to the solution of canagliflozin. The addition of water is carried out at a temperature of about 30° C. to about reflux temperature of the solvent. Surprisingly, it was observed that the addition of more than two equivalents of water provides better yield.

In one embodiment, in step 'd' of the above process an anti-solvent is added to the mixture of step 'c'. The anti-solvent may be selected from the group consisting of esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tertiary butyl ether, tetrahydrofuran, dioxane and the like; ketones such as acetone, ethyl methyl ketone, methyl isobutyl ketone and the like; alcohols such as methanol, ethanol, propanol, isopropanol, butanol, isobutanol, 1-pentanol, 1-octanol and the like; haloalkanes such as dichloromethane, chloroform, ethylene dichloride, and the like; dimethyl sulfoxide; amides such as dimethyl formamide, dimethyl acetamide; water; or mixtures thereof. Preferably, the solvent is methyl tertiary butyl ether.

In one embodiment, the present invention provides a process for the preparation of canagliflozin, a compound of formula I comprising:

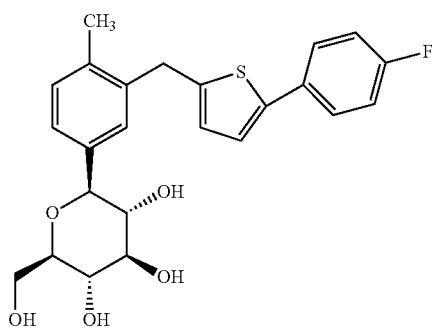

I a) reacting a compound of formula II with a reducing agent

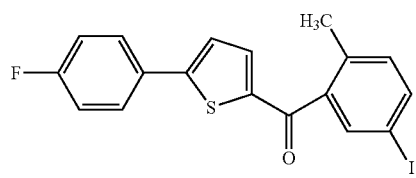

II

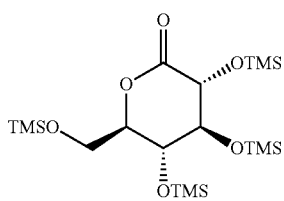

III to obtain a compound of formula III;
b) coupling the compound of formula III with a compound of formula IV

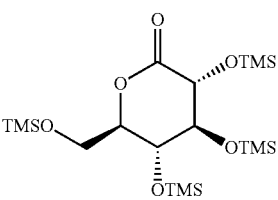

IV

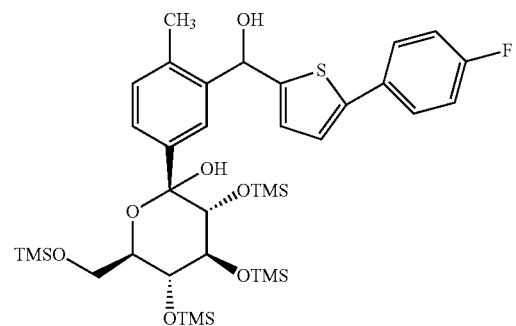

V to obtain a compound of formula V;
c) converting the compound of formula V to a compound of formula VIa

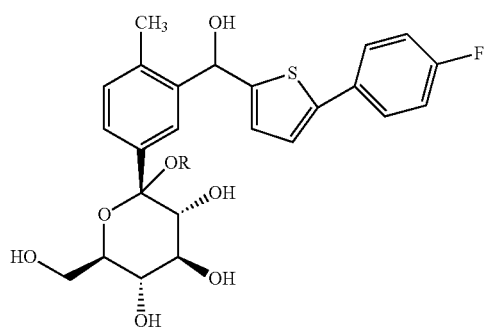

VIa wherein R is an alkyl group selected from the group consisting of methyl, ethyl, propyl, butyl, tert-butyl and the like; and
d) converting the compound of formula VIa to the compound of formula I.

In one embodiment, the present invention provides process for the preparation of compound of formula IV

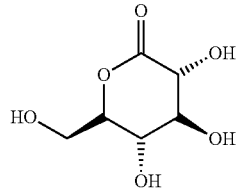

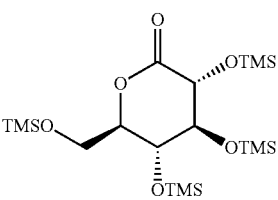

IV comprising reacting D-glucono-1,5-lactone with trimethyl silyl halide such trimethyl silyl chloride. The reaction is carried out in presence of a solvent.

Solvent may be selected from the group consisting hydrocarbons such as toluene, hexane, n-heptane, xylene, cyclohexane and the like; ethers such as tetrahydrofuran, diethyl ether, diisopropyl ether and the like; sulfoxides such as dimethyl sulfoxide; chlorinated solvents such as methylene dichloride, ethylene dichloride, chloroform and the like or mixtures thereof. Preferably, the reaction is carried in a mixtures of solvent.

In one embodiment, the present invention provides a process for the preparation of canagliflozin, a compound of formula I

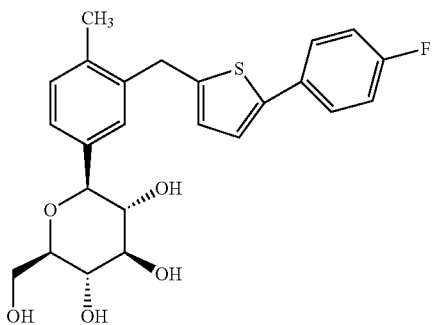

comprising the step of reducing a compound of formula II

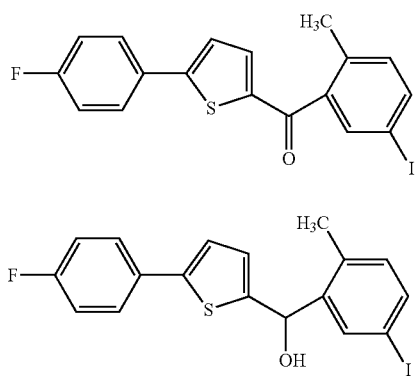

to obtain a compound of formula III.

In one embodiment, the present invention provides a process for the preparation of compound of formula II from 5-iodo-2-methylbenzoic acid by a process as depicted schematically:

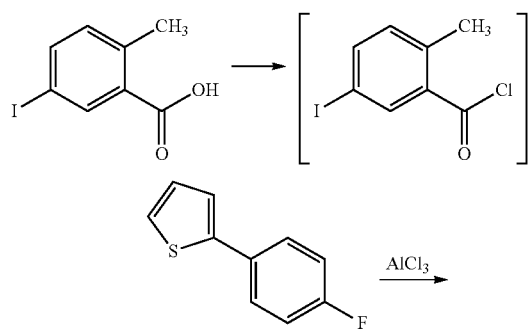

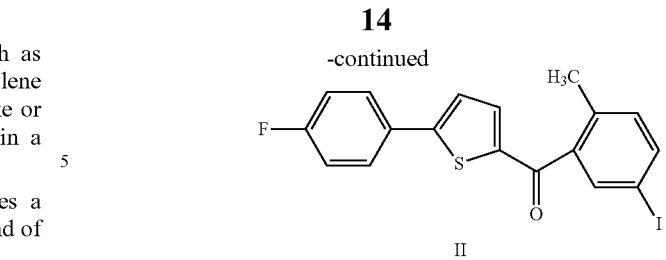

In one embodiment, in the above scheme, the compound of formula II is prepared by condensing the activated derivative of 5-iodo-2-methylbenzoic acid which may be selected from an acid halide or a reactive ester with 2-(4-fluorophenyl)thiophene. The condensation reaction may be carried out in presence of a Lewis acid and a solvent. The lewis acid may be selected from the group consisting of $AlCl_3$, $FeCl_3$, $SnCl_2$, boron trifluoride and the like. The solvent is selected from the group consisting of halogenated solvents such as methylene dichloride, ethylene dichloride, chloroform, carbon tetrachloride and the like; hydrocarbons such as cyclohexane, hexane, toluene, xylene and the like; ethers such as diethyl ether, diisopropyl ether, methyl tertiary butyl ether, tetrahydrofuran and the like; esters such as ethyl acetate, isopropyl acetate and the like. Preferably the solvent is methylene dichloride.

In one embodiment, the condensation reaction is carried out at a temperature of about 5° C. to about 30° C. Preferably, the condensation reaction transpires at a temperature of about 0-5° C.

In one embodiment, the compound of formula II is purified in a solvent.

The solvent may selected from the group consisting of alcohols such as methanol, ethanol, isopropanol, n-propanol, butyl alcohol and the like; esters such as ethyl acetate, isopropyl acetate and the like; water or mixtures thereof.

In one embodiment, the compound of formula II is purified in methanol.

In one embodiment, 2-(4-fluorophenyl)thiophene is prepared by a process comprising lithiating 2-bromothiophene with n-butyl lithium followed by reaction with triethyl borate to obtain 2-thiophene boronic acid, the compound of formula IX. The compound of formula IX may be crystallized from a solvent selected from the group consisting of hexane, toluene, cyclohexane, methylene dichloride, methanol, ethanol, chloroform, isopropanol, propanol, n-butanol or mixtures thereof.

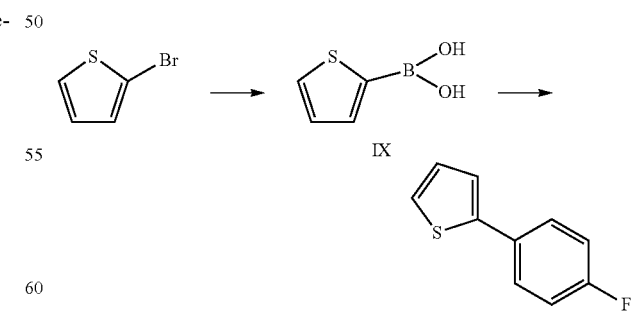

The compound of formula IX is reacted with 4-fluoro bromobenzene in the presence of a palladium catalyst to obtain 2-(4-fluorophenyl)thiophene. The 2-(4-fluorophenyl) thiophene compound obtained may be crystallized from a solvent selected from the group consisting of methylene dichloride, methanol, chloroform, isopropanol, propanol, n-butanol or mixtures thereof.

In one embodiment, 2-(4-fluorophenyl)thiophene is prepared by a process comprising reacting (4-fluorophenyl) boronic acid with 2-bromothiophene.

In one embodiment, the present invention provides a process for the preparation of glucono-1, 5-lactone by a fermentation process of continuous type. The process comprises use of aerobic oxidative fermentation process in conversion of glucose syrup to produce glucono-delta lactone.

In one embodiment, the present invention provides a process for the preparation of glucono-1, 5-lactone by a process of conversion of sodium gluconate to gluconic acid via ion exchange method followed by conversion to glucono-1, 5-lactone.

In one embodiment, the present invention provides a compound selected from the following:

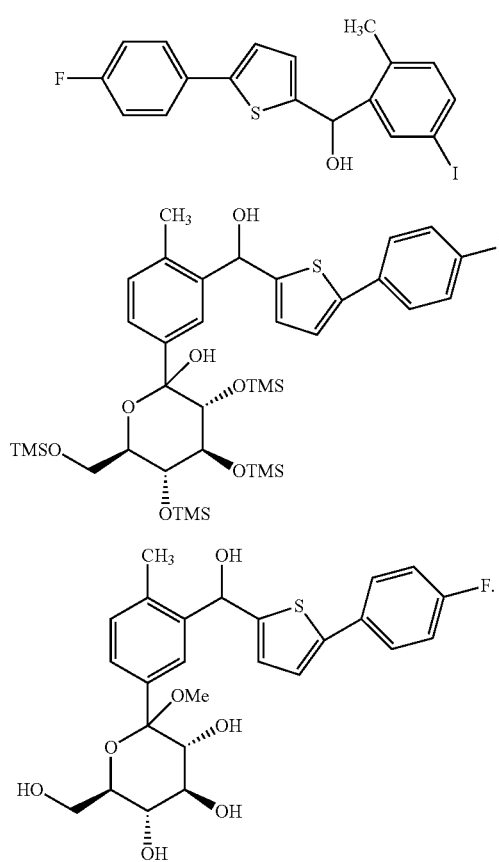

In one embodiment, the present invention provides a method of producing canagliflozin by using a compound selected from the group consisting of

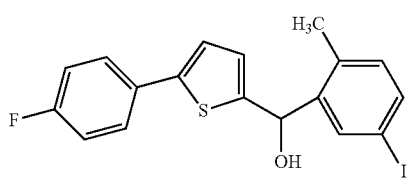

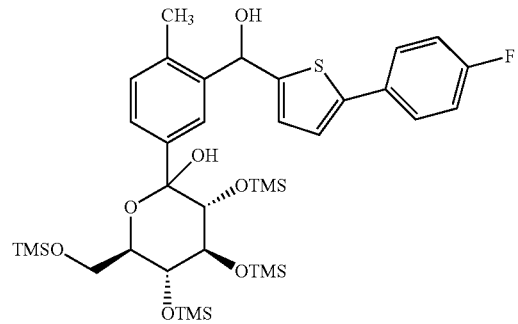

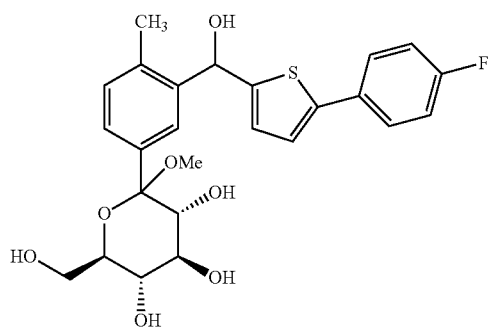

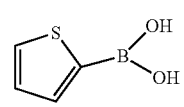

In one embodiment, the present invention provides pharmaceutical compositions comprising canagliflozin or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns. The particle size disclosed here can be obtained by, for example, any milling, grinding, micronizing or other particle size reduction method known in the art to bring the solid state canagliflozin into any of the foregoing desired particle size range.

In one embodiment, the present invention provides canagliflozin having chemical purity of about 99.9% as measured by HPLC.

In one embodiment, the present invention provides canagliflozin having stereochemical purity of about 100% as measured by HPLC.

In one embodiment, canagliflozin obtained is substantially free of 1-(alpha-D-glucopyranosyl)-4-methyl-3-[5-(4-flurophenyl)-2-thienylmethyl] benzene, as measured by HPLC.

In one embodiment, canagliflozin obtained is substantially free of 1-(beta-D-glucopyranosyl)-2-methyl-3-[5-(4-flurophenyl)-2-thienylmethyl] benzene, as measured by HPLC.

In one embodiment, canagliflozin obtained is substantially free of 1-(beta-D-glucopyranosyl)-3-[5-(4-flurophenyl)-2-thienylmethyl] benzene, as measured by HPLC.

In one embodiment, canagliflozin obtained is substantially free of 1-(beta-D-glucopyranosyl)-4-methyl-3-[5-(4-phenyl)-2-thienylmethyl] benzene, as measured by HPLC.

In the present application, the term "substantially free" means an amount which is less than 0.10% w/w with respect to canagliflozin, as determined by high performance liquid chromatography (HPLC).

In one embodiment, the present invention provides amorphous canagliflozin.

In one embodiment, the present invention provides amorphous canagliflozin which is stable and wherein the moisture content does not increase more than 0.4% when exposed for a period of 48 hours to a temperature 25° C. and 60% relative humidity In one embodiment, the present invention provides amorphous canagliflozin which is stable and wherein the moisture content does not increase more than 0.4% when exposed for a period of 48 hours to a temperature 25° C. and 90% relative humidity.

In one embodiment, the present invention provides a process for the preparation of amorphous canagliflozin comprising isolating amorphous canagliflozin from a slurry of canagliflozin in a single solvent.

The solvent may be selected from the group consisting of esters such as ethyl acetate, isopropyl acetate, butyl acetate and the like; hydrocarbons such as cyclohexane, n-heptane, toluene, xylene and the like; ethers such as diisoproyl ether, methyl tertiary butyl ether, tetrahydrofuran and the like; ketone such as acetone, methyl ethyl ketone, methyl i sobutyl ketone and the like; alcohols such as methanol, ethanol, n-propanol, isopropanol; chlorinated solvents such as methylene dichloride, ethylene dichloride, chloroform; nitriles such as acetonitrile, propionitrile and the like and mixtures thereof.

In one embodiment, the present invention provides a process for the preparation of amorphous canagliflozin comprising;
a) preparation of canagliflozin by a process as described above;
b) optionally treating the canagliflozin of step 'a' with an alcoholic solvent;
c) optionally removing the solvent of step 'b';
d) adding hydrocarbon solvent to step 'a' or step 'b' or step 'c'; and
e) isolating amorphous canagliflozin from step 'd'.

The alcoholic solvent in the above step 'b' may be selected from the group consisting of methanol, ethanol, propanol, isopropanol, butanol and the like.

The removal of solvent in the above step 'c' may be accomplished by substantial or complete evaporation of the solvent; or concentrating the solution, cooling the solution if required and filtering the obtained solid. The solution may also be completely evaporated, for example, using a rotavapor, a vacuum paddle dryer or in a conventional reactor under vacuum above about 720 mm Hg.

The hydrocarbon solvent in the above step 'd' may be selected from the group consisting of an aliphatic hydrocarbon or aromatic hydrocarbon. The aliphatic hydrocarbon solvent is selected from the group consisting of n-hexane, cyclohexane and n-heptane and the aromatic hydrocarbon solvent is selected from the group consisting of toluene, benzene, xylene.

The isolation of amorphous canagliflozin in step 'd' may be achieved by spray drying, lyophilisation, filtration, distillation or centrifugation.

In one embodiment, the present invention provides a process for the preparation of amorphous canagliflozin comprising;

a) preparation of canagliflozin by a process as described above;
b) optionally treating the canagliflozin of step 'a' with methanol;
c) optionally removing the solvent of step 'b';
d) adding cyclohexane solvent to step 'a' or step 'b' or step 'c'; and
e) isolating amorphous canagliflozin from step 'd'.

In one embodiment, the present invention provides a process for the preparation of amorphous canagliflozin comprising:
a) subjecting canagliflozin to treatment with a single hydrocarbon solvent; and
b) isolating the amorphous canagliflozin.

The hydrocarbon solvent in step 'a' may be selected from the group consisting of an aliphatic hydrocarbon solvent selected from the group consisting of n-hexane, cyclohexane and n-heptane and aromatic hydrocarbon solvent selected from the group consisting of toluene, benzene and xylene.

In one embodiment, the present invention provides a process for the preparation of amorphous canagliflozin comprising:
a) subjecting canagliflozin to treatment with cyclohexane; and
b) isolating the amorphous canagliflozin.

In one embodiment, the present invention provides a process for the preparation of amorphous canagliflozin comprising converting crystalline canagliflozin (1-S) to amorphous canagliflozin.

In one embodiment, the present invention provides amorphous canagliflozin characterized by X-ray diffraction (XRD) spectrum as depicted in FIG. 4.

In one embodiment, the present invention provides amoprhous canagliflozin characterized by Differential Scanning calorimetric (DSC) thermogram having an endothermic peak at about 59.9±2° C. and 191.83±2° C.

In one embodiment, the present invention provides amorphous canagliflozin characterized by Differential Scanning calorimetric (DSC) thermogram which is substantially in accordance with FIG. 5.

In one embodiment, the present invention provides amorphous canagliflozin characterized by Thermogravimetric analysis (TGA) profile showing a weight loss of about about 2% to about 3% weight loss from about 50° C. to about 100° C.

In one embodiment, the present invention provides amorphous canagliflozin characterized by Thermogravimetric analysis thermogram, which is substantially in accordance with FIG. 6.

In one embodiment, the present invention provides process for the preparation of crystalline canagliflozin hemihydrate comprising converting crystalline canagliflozin to crystalline canagliflozin hemihydrate.

In one embodiment, the present invention provides process for the preparation of crystalline canagliflozin hemihydrate comprising converting amorphous canagliflozin to crystalline canagliflozin hemihydrate without seeding.

In one embodiment, the present invention provides process for the preparation of crystalline canagliflozin hemihydrate comprising converting crystalline canagliflozin to crystalline canagliflozin hemihydrate without seeding.

In one embodiment, the present invention provides process for the preparation of crystalline can agliflozin hemihydrate comprising:

a) treating canagliflozin with a solvent to obtain a solution or a suspension;
b) optionally adding an anti-solvent to step 'a'; and
c) isolating crystalline canagliflozin hemihydrate.

The solvent in step 'a' may be selected from the group consisting of halogenated hydrocarbons such as methylene chloride, ethylene chloride, chloroform and carbon tetrachloride; alcohols such as methanol, ethanol, 1propanol, isopropanol, tert-butanol; ketones such as acetone, methyl isobutyl ketone; esters such as ethyl acetate, isopropyl acetate and butyl acetate; amides such as formamide, N,N-dimethylformamide, N,N-dimethylacetamide; dimethyl sulfoxide; nitrile such as acetonitrile, propionitrile; ethers such as diethyl ether, diisopropyl ether, methyl t-butyl ether, 1,4-dioxane, tetrahydrofuran; hydrocarbons such as heptane, benzene, toluene, cyclohexane, methyl cyclohexane and toluene, water; or mixtures thereof.

The anti-solvent in step 'b' may be selected from the group consisting of water, alcohols such as methanol, ethanol, isopropanol, propanol; hydrocarbons such as heptane, benzene, toluene, cyclohexane, methyl cyclohexane and toluene; esters such as ethyl acetate, isopropyl acetate and butyl acetate; ethers such as diethyl ether, diisopropyl ether, t-butyl methyl ether; and the like or mixtures thereof.

The canagliflozin used in the preparation of crystalline canagliflozin hemihydrate may be crystalline canagliflozin or amorphous canagliflozin.

In one embodiment, the present invention provides process for the preparation of crystalline canagliflozin hemihydrate comprising isolating crystalline canagliflozin hemihydrate canagliflozin from a mixture of acetone and water without seeding.

In one embodiment, the present invention provides crystalline canagliflozin monohydrate.

In one embodiment, the present invention provides crystalline canagliflozin monohydrate characterized by X-ray diffraction (XRD) spectrum having peak reflections at about 13.0, 15.7, 17.6, 20.0 and 25.0±0.2 degrees 2 theta.

In one embodiment, the present invention provides crystalline canagliflozin monohydrate characterized by X-ray diffraction (XRD) spectrum having peak reflections at about 6.7, 13.0, 15.7, 17.6, 20.0, 25.0 and 33.5±0.2 degrees 2 theta.

In one embodiment, the present invention provides crystalline canagliflozin monohydrate characterized by X-ray diffraction (XRD) spectrum as depicted in FIG. 1.

In one embodiment, the present invention provides crystalline canagliflozin monohydrate characterized by Differential Scanning calorimetric (DSC) thermogram having an endothermic peak at about 62±2° C.

In one embodiment, the present invention provides crystalline canagliflozin monohydrate characterized by Differential Scanning calorimetric (DSC) thermogram, which is substantially in accordance with FIG. 2.

In one embodiment, the present invention provides crystalline canagliflozin monohydrate characterized by thermogravimetric analysis profile showing about 3% to about 5% weight loss from about 50° C. to about 150° C.

In one embodiment, the present invention provides crystalline canagliflozin monohydrate characterized by TGA thermogram, which is substantially in accordance with FIG. 3.

In one embodiment, the present invention relates to crystalline canagliflozin monohydrate characterized by having a water content ranging from 3% to about 5% as measured using Karl Fischer method.

In one embodiment, the present invention provides crystalline canagliflozin monohydrate characterized by X-ray Diffraction (XRD) spectrum having peak reflections at about 13.0, 15.7, 17.6, 20.0 and 25.0±0.2 degrees 2 theta and Differential Scanning calorimetric (DSC) thermogram having an endotherm peak at about 62±2° C.

In one embodiment, the present invention provides crystalline canagliflozin monohydrate characterised by X-ray Diffraction (XRD) spectrum having peak reflections at about 13.0, 15.7, 17.6, 20.0 and 25.0±0.2 degrees 2 theta, which is substantially in accordance with FIG. 1 and differential scanning calorimetric (DSC) thermogram having an endotherm peak at about 62±2° C., which is substantially in accordance with FIG. 2.

The theoretical water content of the crystalline canagliflozin monohydrate of the present invention is about 3.9%.

In one embodiment, the present invention provides crystalline canagliflozin monohydrate further characterized by thermogravimetric analysis (TGA) thermogram, showing a weight loss of about 3 to about 5% determined over the temperature range of 50° C. to 100° C. and heating rate 10° C./min, which is substantially in accordance with FIG. 3.

In one embodiment, the present invention provides crystalline canagliflizon monohydrate further characterized by thermogravimetric analysis (TGA) thermogram, showing a weight loss of about 3 to about 5% determined over the temperature range of 50° C. to 100° C. and heating rate 10° C./min, which is substantially in accordance with FIG. 3 and DSC analysis.

In one embodiment, the present invention provides crystalline canagliflozin monohydrate characterized by at least one of the following:
a) X-ray Diffraction (XRD) spectrum having peak reflections at about 13.0, 15.7, 17.6, 20.0 and 25.0±0.2 degrees 2 theta.
b) differential Scanning calorimetric (DSC) thermogram having an endothermic peak at about 62±2° C.
c) thermogravimetric analysis profile showing about 3% to about 5% weight loss from about 50° C. to about 100° C.

In one embodiment, the present invention provides a process for the preparation of canagliflozin monohydrate comprising isolating from a mixture of water and an organic solvent.

In one embodiment, the present invention provides a process for the preparation of canagliflozin monohydrate comprising isolating from a mixture of water and an organic solvent without seeding.

In one embodiment, the organic solvent may be selected from the group consisting of esters such as ethyl acetate, isopropyl acetate and the like; ketones such as acetone, methyl ethyl ketone and the like; hydrocarbons such as toluene, hexane, cyclohexane, xylene, n-heptane and the like; sulfoxide such as dimethyl sulfoxide and the like, water or mixtures thereof.

In one embodiment, the present invention provides a process for the preparation of crystalline canagliflozin monohydrate by solvent-anti solvent method.

In one embodiment, the solvent may be selected from the group consisting of esters such as ethyl acetate, methyl acetate, isopropyl acetate and the like; ketones such as acetone, methyl isobutyl ketone and the like; hydrocarbons such as toluene, xylene, heptane, hexane and the like; water or a mixture of thereof In one embodiment anti-solvent may be selected from the group consisting of heptane and water.

In one embodiment, the present invention provides preparation of crystalline can agliflozin monohydrate using acetone as solvent and water as an anti-solvent.

In one embodiment, the present invention provides a process for the preparation of crystalline canagliflozin monohydrate comprising dissolving canagliflozin in acetone and adding water as an anti-solvent to precipitate crystalline canagliflozin monohydrate.

In one embodiment, the addition of water to a solution of canagliflozin in acetone is carried out a temperature of about 25 to about 30° C.

In one embodiment, the reaction mass is stirred for a period of about 3 to 8 hours.

In one embodiment, crystalline canagliflozin monohydrate precipitated is isolated by methods such as filtration, centrifugation and the like.

In one embodiment, the present invention provides a process for the preparation of crystalline canagliflozin monohydrate comprising isolation of crystalline canagliflozin monohydrate from a mixture of acetone and water without seeding.

In one embodiment, the present invention provides a process for the preparation of crystalline canagliflozin monohydrate comprising isolating from a mixture of ethyl acetate and water.

In one embodiment, the present invention provides a process for the isolation of crystalline canagliflozin monohydrate from a solvent system comprising of ethyl acetate and water and no additional solvent.

In one embodiment, the present invention provides a process for the preparation of crystalline canagliflozin monohydrate comprising:
a) treating canagliflozin with ethyl acetate;
b) heating the above reaction mixture of step "a";
c) addition of water to above step "b";
d) cooling the above mixture of "c";
e) isolating the precipitated crystalline canagliflozin monohydrate.

In one embodiment, in step a) of the above process canagliflozin is treated with ethyl acetate.

In one embodiment, in step b) of the above process the slurry of canagliflozin in ethyl acetate is heated to obtain a solution.

In one embodiment, the slurry of canagliflozin in ethyl acetate is heated to a temperature of about 35-40° C.

In one embodiment, in step c) of the above process water is added to a solution of canagliflozin.

In one embodiment, the addition of water to a solution canagliflozin in ethyl acetate is carried at a temperature of about 35-40° C.

In one embodiment, the reaction mixture comprising canagliflozin, ethyl acetate and water is stirred for a period of about 30 min to about 90 min.

In one embodiment, in step d) of the above process the reaction mixture comprising canagliflozin, ethyl acetate and water is cooled to a temperature of about −5 to about 25° C. Preferably, the reaction mixture is cooled to a temperature of about 0-5° C.

In one embodiment, in step e) of the above process crystalline canagliflozin monohydrate, precipitated from a mixture of ethyl acetate and water is isolated by methods such as filtration, centrifugation and like.

In one embodiment, the present invention relates to a process for the preparation of crystalline canagliflozin monohydrate comprising isolating crystalline canagliflozin monohydrate from a mixture of ethyl acetate and water without seeding.

In one embodiment, the present invention provides a process for the preparation of crystalline canagliflozin monohydrate, comprising isolating crystalline canagliflozin monohydrate from an aqueous solution.

In one embodiment, the present invention provides a process for the preparation of crystalline canagliflozin monohydrate, comprising:
a) treating canagliflozin with water;
b) cooling the reaction mixture of step b); and
c) isolating the precipitated crystalline canagliflozin monohydrate In one embodiment, in step a) of the above process canagliflozin is treated with water.

In one embodiment, in step b) of the above process the slurry of canagliflozin in water is cooled to a temperature of about −5 to about 20° C. Preferably, the slurry is cooled to a temperature of about 0-5° C.

In one embodiment, in step c) of the above process, the precipitated crystalline canagliflozin monohydrate is filtered and isolated by methods such as filtration, centrifugation and the like.

In one embodiment, the present invention relates to a process for the preparation of crystalline canagliflozin monohydrate comprising isolating from an aqueous solution without seeding.

In one embodiment, the present invention provides amorphous canagliflozin.

In one embodiment, the present invention provides amorphous canagliflozin as a foamy solid.

In one embodiment, canagliflozin, the starting material used in the preparation of crystalline canagliflozin monohydrate, is amorphous canagliflozin.

In one embodiment, the present invention provides canagliflozin sesquihydrate.

In one embodiment, the canagliflozin sesquihydrate is characterized by thermo gravimetric analysis (TGA) thermogram, showing a weight loss of about 5.1% to about 6.1% determined over the temperature range of 50° C. to 100° C. and heating rate 10° C./min.

In one embodiment, the present invention relates to crystalline canagliflozin sesquihydrate characterized by having a water content ranging from 5.1% to about 6.1% as measured using Karl Fischer method.

Instrumental Settings for HPLC:

Reagents and Solvents: Potassium dihydrogen phosphate, o-phosphoric acid, Methanol, Acetonitrile, Water. Column: Hypersil BDS C8, 250×4.6 mm, 5μ.

Instrumental Settings for XRPD:

The measurements were performed on Philips X-Ray Diffractometer model XPERT-PRO (PANalytical) Detector: X'celerator [1] using Cu lamp with type and wavelength of the X-ray radiation: K-Alpha1 [A] and 1.54060 under the following conditions: Generator settings: 40 mA/45 kV, Time per step: 50, Step size: 0.0170, Peak width 2.00 and start angle (° 2 theta) 2.0 and End angle: 50.0, Scan type: continuous; measurement performed at 25° C. The XRPD instrument is calibrated using NIST SRM 6-40C silicon standard and NIST SRM 1976 Alumina.

Instrumental Settings for DSC:

The DSC thermogram was measured by a Differential Scanning calorimeter (DSC 822, Mettler Toledo) at a scan rate of 10° C. per minute in the temperature range of range is "30° C. to 300° C.". The DSC module was calibrated with Indium and zinc standard.

Instrumental Settings for TGA:

Instrument Name: TGA Q 500; Method: 5-8 mg of sample was taken in platinum pan and heated at 10° C./minute from room temperature to 250° C.

Method for Measuring the Water Content

About 10 g canagliflozin was exposed to 25° C. and 60% relative humidity and 25° C. and 90% relative humidity conditions. About 300 mg of sample was withdrawn each time at the timely intervals of 1 hr, 2 hrs, 4 hrs, 8 hrs, 12 hrs, 24 hrs and 48 hrs from the conditions and tested for description and water content by KF. The water content was calculated by the following formula:

$$\text{water content (\%)} = \frac{\text{Burrette reading} \times K.F.\ \text{factor}}{\text{weight of sample in mg}} \times 100$$

The following examples are provided to enable one skilled in the art to practice the invention and are merely illustrative of the invention. The examples should not be read as limiting the scope of the invention.

EXAMPLES

Example 1: Preparation of Compound of Formula-II

A mixture of 5-iodo-3-methyl benzoic acid (100 gm), methylene dichloride (500 ml) and dimethyl formamide (1.2 ml) was stirred and to this oxalyl chloride (42.4 ml) was added at 25-30° C. The reaction mixture was stirred for a period of 4 hr at a temperature of 25-30° C. The reaction mixture was distilled and to the residue methylene dichloride were added to obtain a clear solution. The reaction mixture was cooled to 0-5° C. To the reaction mixture, aluminium chloride (55.83 gm) and 2-(4-fluorophenyl) thiophene (67.93 gm) in methylene dichloride at 0-5° C. was added. The reaction mixture was stirred and to this mixture water was added and layers separated. The organic layer was distilled under vacuum at 35-40° C. and to this methanol was added to obtain a slurry. The slurry was stirred for 30 min at 25-30° C. followed by filtration and washing with methanol. The product was dried at 40-45° C. to obtain 152 gm of the product.

1H NMR (300 Mhz, DMSO $d_6$) having peaks at 2.4, 7.09, 7.17, 7.26, 7.40, 7.73-7.81, 7.83, 8.01.

Example 2: Preparation of Compound [5-(4-fluorophenyl)thiophen-2-yl] (5-iodo-2-methylphenyl) methanol (III)

To a mixture of [5-(4-fluorophenyl)thiophen-2-yl](5-iodo-2-methylphenyl)methanone (150 gm) in methylene dichloride (750 ml) sodium borohydride (20.26 gm) and methanol (150 ml) were added at 25-30° C. over a period of 90-120 min. The reaction mixture was stirred for 2 hrs. To the reaction mixture, water was added followed by addition of 1:1 aq. HCl at 25-30° C. The reaction mixture was stirred and layers were separated. The organic layer was distilled under vacuum. To the residue n-heptane was added to obtain a slurry. The reaction mixture was stirred for 1.0 hr and filtered and washed with n-heptane. The product was dried at 40-45° C. to obtain 142.5 gm of the title product.

1H NMR (300 Mhz, DMSOd$_6$) having peaks at 2.18, 5.97, 6.29, 6.79, 6.94, 7.16-7.26, 7.52, 7.58-7.62, 7.85.

Examples 3: Preparation of Compound [5-(4-fluorophenyl)thiophen-2-yl] (5-iodo-2-methylphenyl) methanol (III)

The above reaction was repeated without treatment with aq hydrochloric acid.

Example 4: Preparation of 2, 3, 4, 6-tetra-O-trimethylsilyl-β-D-gluconolactone (IV)

A mixture of D-glucono-1,5-lactone (30 g), THF (tetrahydrofuran, 300 ml) and N-methylmorpholine (130 ml) was cooled to a temperature of about 0 to −10° C. Trimethyl silylchloride (130 ml) was added. The reaction mass was stirred and maintained for a period of about 60 min. The temp of the reaction mass was increased to 25-30° C. The reaction mass was maintain for 4-5 hrs and cooled to 0-10° C. To the reaction mass toluene and water were added. The temperature of the reaction mass was raised to 10-15° C. The layers were separated and toluene layer was washed with sodium dihydrogen phosphate solution in water. The toluene layer was dried over sodium sulphate, filtered and distilled under vacuum to obtain 70 g of title product. GC purity: 95.14%

Example 5: Preparation of 1-(1-methoxyglucopyranosyl)-4-methyl-3-(5-(4-fluorophenyl)-2-thienylhydroxymethyl)benzene (VI)

A mixture of [5-(4-fluorophenyl)thiophen-2-yl](5-iodo-2-methylphenyl)methanol (15 g), tetrahydrofuran (75 ml), 2, 3, 4, 6-tetra-O-trimethylsilyl-β-D-gluconolactone (21.43 g) and toluene (75 ml) under nitrogen was cooled to −60 to about −70° C. To the reaction mixture n-butyl lithium (75 ml) in hexane was added. The reaction mixture was maintained for 2 hrs. To this reaction mass methanesulfonic acid (13.6 g) in methanol solution (75 ml) was added. The temp of the reaction mixture was raised to 25-30° C. and maintained for 5-6 hrs. The reaction mass was quenched with saturated sodium bicarbonate solution. To the reaction mass ethyl acetate was added. The layers were separated. The ethyl acetate layer was dried on sodium sulphate, filtered and distilled under vacuum. To the residue toluene (150 ml) was added and stirred to obtain a solution. To this n-Hexane (500 ml) was added. The reaction mass was maintained for 1-2 hrs at 25-30° C. The product was isolated by filtration and dried at 25-30° C. under vacuum to obtain 14 gms of the product. 1H-NMR (DMSO, d6, 300 MHz): 2.24, 2.9, 3.55, 3.75, 4.53, 4.66-4.70, 4.96, 5.68, 6.82-6.91, 7.14-7.24, 7.35, 7.60-7.65.

Example 6: Preparation of Canagliflozin (I)

A mixture of 1-(1-methoxyglucopyranosyl)-4-methyl-3-(5-(4-fluorophenyl)-2-thienylhydroxymethyl) benzene (10 g) and methylene chloride (100 ml) was cooled to a temperature of about −70 to about −75° C. To the reaction mass triethylsilane (8 ml) was added slowly. The reaction mass was maintained for a period of about 15 to 30 min. To the reaction mass boron trifluoride diethyl etherate (10 ml) was added. The temp of the reaction mass was raised to 0° C. The reaction mass was maintained for a period of about 2-3 hrs. To the reaction mass saturated sodium bicarbonate solution was added. The reaction mass was maintained for a period of about 30 to 90 min. The reaction mass was distilled under vacuum. To the reaction mass ethyl acetate and water were added. The ethyl acetate layer was separated, washed with water and brine solution. Ethyl acetate layer was dried on sodium sulphate, treated with activated carbon and filtered. The filtrate was distilled under vacuum to obtain a foamy solid.

Example 7: Preparation of Crystalline Canagliflozin canagliflozin (100 g) was dissolved in ethyl acetate (300 ml) to get clear solution. To this solution methyl tertiary butyl ether (1200 ml) and water (10 ml) were added. The mixture was stirred at 25-30° C. for 12 hrs. Filter solid, washed with methyl tertiary butyl ether to obtain 60 gm of title product.

Example 8: Preparation of Crystalline Canagliflozin Monohydrate

The solid obtained in example 6 was dissolved in acetone (14 ml) by stirring at a temperature of about 25-30° C. To this solution water (105 ml) was added slowly at 25-30° C. The reaction mass was maintained for 4-5 hrs at 25-30° C. The crystalline canagliflozin monohydrate precipitated was isolated by filtration and dried at 25-30° C. under vacuum to obtain 7 gms of title product. HPLC purity: 99.99%, stereochemical purity: 100% XRD of crystalline canagliflozin monohydrate: 13.0, 17.8, 20.0 and 24.6±0.2 degrees 2 theta

| Po. [°2Th] | d-spacing [A°] | Rel. Int [%] | Po. [°2Th] | d-spacing [A°] | Rel. Int [%] |
|---|---|---|---|---|---|
| 3.5 | 24.8 | 3.42 | 17.8 | 5.01 | 40.77 |
| 6.7 | 13.09 | 8.96 | 20 | 4.42 | 100 |
| 13 | 6.77 | 29.31 | 24.5 | 3.55 | 31.81 |
| 15.7 | 5.62 | 28.22 | 33.4 | 2.67 | 4 |

Example 9: Preparation of Crystalline Canagliflozin Hemihydrate(I)

The solid obtained in example 7 was dissolved in ethyl acetate (40 ml). To this solution diethyl ether (150 ml) and water (1.0 ml) was added at 25-30° C. The reaction mass was maintained for a period of about 6 to about 8 hrs. The product was isolated by filtration and dried at under vacuum to obtain 6 gm of title product.

Example 10: Preparation of Crystalline Canagliflozin Monohydrate

A mixture of amorphous canagliflozin (10 g) in water (150 ml) was maintained for a period of about 2-3 hrs at 25-30° C. The reaction mixture was cooled to 5-10° C. and maintained for a period of about 2-3 hrs. Crystalline canagliflozin monohydrate was isolated by filtration and dried at 25-30° C. under vacuum to obtain 10 gm of title product.

Example 11

Preparation crystalline canagliflozin monohydrate: A mixture of amorphous canagliflozin (10 g) in ethyl acetate (20 ml) was prepared at a temperature of about 25-30° C. The reaction mixture was heated to 35-40° C. and maintained till a clear solution was obtained. To this water (600 ml) was added at 35-40° C. and the reaction mass was maintained for a period of about 30 min to about 90 min at 35-40° C. The reaction mixture was then cooled to 0-5° C. and maintained for about 2-3 hrs. Crystalline canagliflozin monohydrate was isolated by filtration and dried at 25-30° C. under vacuum to obtain 9 gm of title product.

Example 12: Preparation Crystalline Canagliflozin Monohydrate

A mixture of amorphous canagliflozin (7.0 gms) and acetone (14 ml) was stirred to obtain a clear solution at 25-30° C. To this water (105 ml) was added slowly through the addition funnel at 25-30° C. The reaction mass was maintain for 17 hrs at 25-30° C. The solid was filtered and dried at 25-30° C. under vacuum to obtain 6 gm of title product.

Example 13: Preparation Crystalline Canagliflozin Monohydrate

A mixture of amorphous canagliflozin (2.0 gm) and acetone (20 ml) was stirred to obtain a clear solution. To this water (60 ml) was added slowly at 25-30° C. The reaction mass was maintained for 15-20 min at 25-30° C. The oil from the mixture was separated and charged in a clean flask. To this water was added slowly at 25-30° C. The reaction mass was maintained for 30-60 min at 25-30° C. Crystalline canagliflozin monohydrate was isolated by filtration and dried at 25-30° C. under vacuum to obtain 1.7 gms of title product.

Example 14: Preparation of Canagliflozin (I)

A mixture of 5-(4-fluorophenyl)thiophen-2-yl](5-iodo-2-methylphenyl) methanol (10 gm), tetrahydrofuran (25 ml), 2, 3, 4, 6-tetra-O-trimethylsilyl-β-D-gluconolactone (33 gm) and toluene (25 ml) was cooled to −60 to about −70° C. To the reaction mass n-butyl lithium (70 ml) 1.6 M solution in hexane was added. The reaction mixture was maintained and to this methansulfonic acid (65 gm) in methanol was added. The temp of the reaction mixture was raised to 20-30° C. and maintained for 17 hrs. The reaction mass was quenched with sodium bicarbonate. Layers were separated. The aqueous layer was extracted with methylene dichloride. The methylene dichloride layer was washed with brine solution and distilled under vacuum at 35-40° C. to obtain oily mass. To the obtained oily mass methylene dichloride was added and stirred to get clear solution. To the reaction mass triethylsilane (15 ml) was added. The reaction mass was cooled to a temperature of about −60 to −70° C. and borontrifluoride diethyl etherate (10 ml) was added slowly. The reaction mass was maintained for a period of about 2 hrs. After completion of reaction, reaction mass was quenched with sodium bicarbonate solution and methylene dichloride was distilled from the reaction mixture and ethyl acetate was added and layers were separated. The ethyl acetate layer was distilled under vacuum to obtain oily mass. To this ethyl acetate (24 ml) was added to get clear solution. To this mixture methyl tert-butyl ether (120 ml) and water was added (1 ml) and stirred for 12 hrs at 20-30° C. The solid obtained was filtered, washed with methyl tert-butyl ether and dried to get 5-6 gm of product.

A mixture of above product and ethyl acetate (25 ml) was heated to 40-45° C. to get clear solution. To this solution was added methyl tert-butyl ether (75 ml) and water (0.5 ml). The solution was cooled gradually to 25-30° C. and stirred for 12 hrs. Filtered the product and washed with methyl tert-butyl ether to get wet cake of the product, wet weight.: 4-5 gm. HPLC purity: 99.60%

1H NMR (300 Mhz, DMSOd$_6$) having peaks at 2.25, 3.19, 3.36, 3.68, 3.95, 4.12, 4.45, −4.74, 4.95, 6.79, 7.13-7.27, 7.59. Water Content: 2.12%, Melting point: 96.6° C.-98.3° C., FT-IR (KBr): 3590, 3549, 3477, 3409, 3273 (OH), 2902, 1508, 1232, DSC: 104.07° C.

Example 15: Preparation of Canagliflozin Amorphous

A mixture of amorphous canagliflozin (40 g) and methanol (240 ml) was stirred at 25-30° C. to get clear solution. The solution was filtered over hyflo bed and distilled under vacuum at 35-40° C. to get foamy solid. To this foamy solid cyclohexane (400 ml) was added at 25-30° C. and stirred for 2 hrs. The product was filtered, washed with cyclohexane and dried at 40-45° C. title product. HPLC purity: 99.95%, DSC: 60.25° C., Content of cyclohexane: 1379 ppm.
Results of Hygroscopic Study for Canagliflozin Obtained as Per Example 16

|  | Time Point | | | | | | | |
| --- | --- | --- | --- | --- | --- | --- | --- | --- |
|  | Initial | 1 hr | 2 hrs | 4 hrs | 8 hrs | 12 hrs | 24 hrs | 48 hrs |
|  | 25° C./60% RH | | | | | | | |
| Description | Off white powder | Off white powder | Off white powder | Off white powder | Off white powder | Off white powder | Off white powder | Off white powder |
| Moisture content by KF (%) | 2.19 | 2.22 | 2.29 | 2.33 | 2.35 | 2.39 | 2.42 | 2.49 |
|  | 25° C./90% RH | | | | | | | |
| Description | Off white powder | Off white powder | Off white powder | Off white powder | Off white powder | Off white powder | Off white powder | Off white powder |
| Moisture content by KF (%) | 2.19 | 2.36 | 2.48 | 2.52 | 2.69 | 2.87 | 3.17 | 3.48 |

Example 16: Preparation of Crystalline Canagliflozin Hemihydrate

Method 1:
To a solution of amorphous canagliflozin in acetone was added water dropwise. The reaction mass was stirred for 18 hrs at 25-30° C. The product was filtered and washed with acetone and water and dried under vacuum to obtain 2.5 gm of titled product. Water content: 2.70%.

Method 2:
To a solution of amorphous canagliflozin in ethyl acetate was added diethyl ether and water. The reaction mixture stirred at 25-30° C. for 18 hrs The product was filtered and washed with ethyl acetate and diethyl ether to obtain 2.7 gm of titled product. Water content: 2.66%, HPLC purity: 99.95%.

Example 17: Preparation of Amorphous Canagliflozin

A mixture of crystalline canagliflozin hemihydrate and methanol was stirred at 25-30° C. to get clear solution. The solution was filtered and distilled under vacuum to obtain foamy solid. To this foamy solid cyclohexane was added at 25-30° C. The product was filtered and washed with cyclohexane to obtain title product, dried at 40-45° C.; HPLC purity: 99.49%

Example 18: Preparation of Crystalline Canagliflozin canagliflozin (100 g) was dissolved in ethyl acetate (300 ml) to get clear solution. To this solution methyl tertiary butyl ether (1200 ml) and water (8 ml) were added. The mixture was stirred at 25-30° C. for 12 hrs. The solid was filtered and washed with methyl tertiary butyl ether to obtain 52 gm of title product.

The invention claimed is:

1. A compound selected from the following:

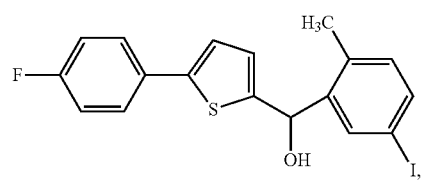

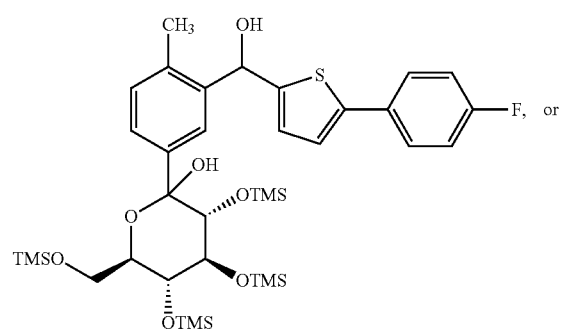

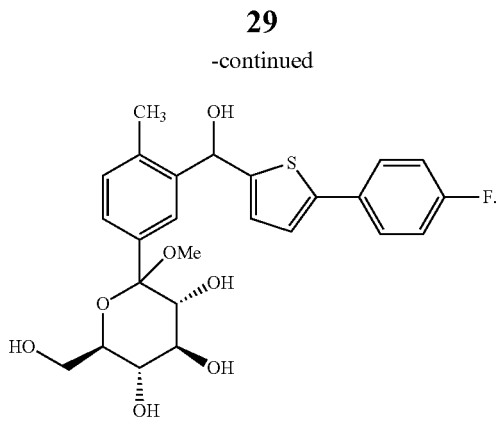

2. A process for the preparation of canagliflozin, a compound of formula I, comprising:

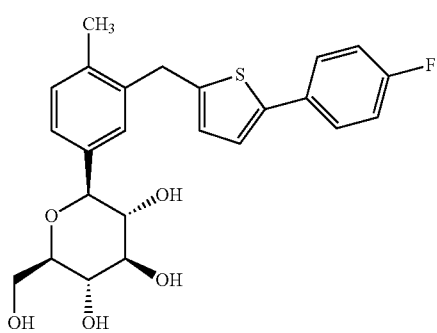

a) reacting a compound of formula II with a reducing agent

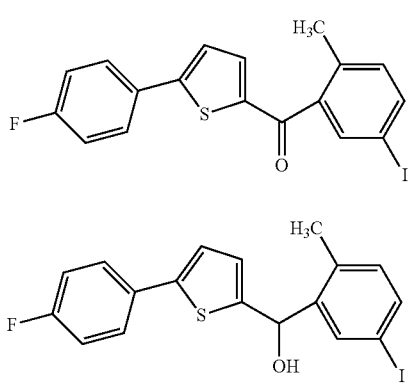

to obtain a compound of formula III;

b) coupling the compound of formula III with a compound of formula IV

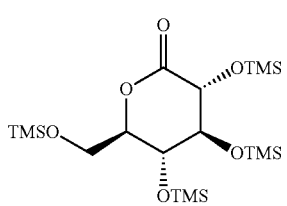

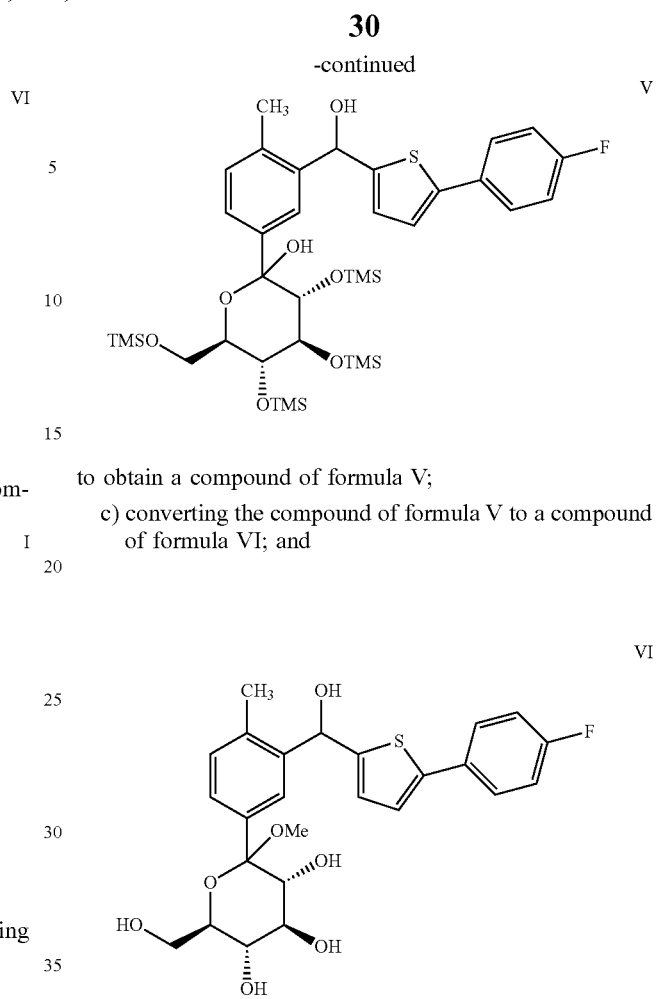

to obtain a compound of formula V;

c) converting the compound of formula V to a compound of formula VI; and d) converting the compound of formula VI to the compound of formula I.

3. The process as claimed in claim 2, wherein in step (a) the reducing agent is selected from the group consisting of diborane, diazene, sodium borohydride potassium borohydride, lithium aluminium hydride and diisobutyl aluminium hydride and aluminum hydride.

4. The process as claimed in claim 2, wherein in step (a) the compound of formula II is reduced to the compound of formula III in the absence of a Lewis acid.

5. The process as claimed in claim 2, wherein in step (b) the coupling reaction is carried out in presence of a has selected from the group consisting of n-butyl lithium, sec-butyl lithium, sodium hydride, potassium hydride and a isopropylmagnesium chloride.lithium chloride complex.

6. The process as claimed in claim 2, wherein in step (c) the compound of formula V is converted to the compound of formula VI in the presence of an acid.

7. The process as claimed in claim 2, wherein in step (d) the compound of formula VI is converted to the compound of formula I by treating the compound of formula VI with a reducing agent.

8. The process as claimed in claim 7, wherein the reducing agent is triethyl silane.

9. A method of producing canagliflozin, a compound of formula I,

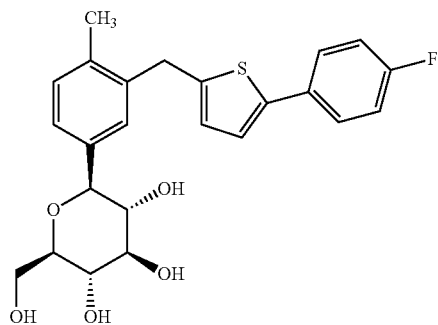

I by a process comprising any of the following steps:
  a) converting a compound of formula IX to a compound of formula II;

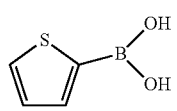

IX

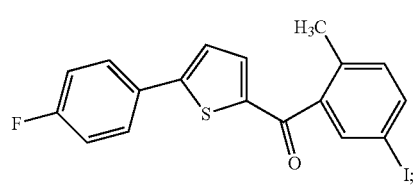

II or
  b) reacting a compound of formula II with a reducing agent to obtain a compound of formula III;

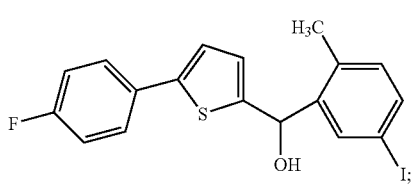

III or
  c) coupling a compound of formula III with a compound of formula IV to obtain a compound of formula V;

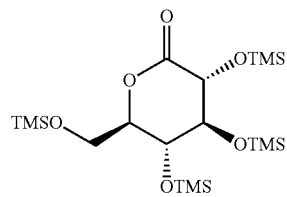

IV

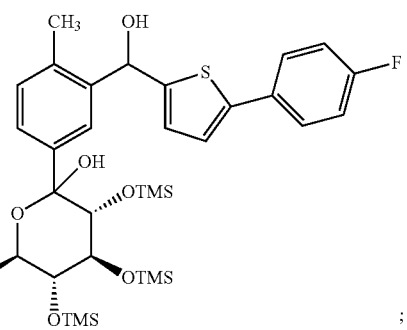

V or
  d) converting a compound of formula V to a compound of formula VI;

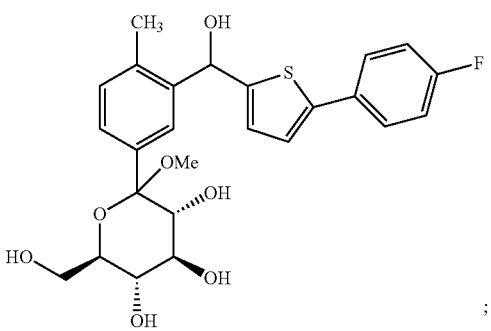

VI or
  e) converting a compound of formula VI to the compound of formula I.

* * * * *